United States Patent
Freesmeyer et al.

(10) Patent No.: US 11,701,439 B2
(45) Date of Patent: Jul. 18, 2023

(54) DAZA CHELATORS AS LIGANDS IN LIVER IMAGING

(71) Applicant: X-NUCLEAR DIAGNOSTICS GMBH, Erfurt (DE)

(72) Inventors: Martin Freesmeyer, Jena (DE); Julia Greiser, Jena (DE)

(73) Assignee: X-NUCLEAR DIAGNOSTICS GMBH, Erfurt (DE)

( * ) Notice: Subject to any disclaimer, the term of this patent is extended or adjusted under 35 U.S.C. 154(b) by 87 days.

(21) Appl. No.: 16/771,696

(22) PCT Filed: Dec. 10, 2018

(86) PCT No.: PCT/EP2018/084107
§ 371 (c)(1),
(2) Date: Jun. 11, 2020

(87) PCT Pub. No.: WO2019/115429
PCT Pub. Date: Jun. 20, 2019

(65) Prior Publication Data
US 2021/0069357 A1 Mar. 11, 2021

(30) Foreign Application Priority Data
Dec. 11, 2017 (DE) .................... 10 2017 129 405.8

(51) Int. Cl.
*A61K 51/04* (2006.01)
*C07D 243/08* (2006.01)

(52) U.S. Cl.
CPC ........ *A61K 51/0482* (2013.01); *C07D 243/08* (2013.01)

(58) Field of Classification Search
CPC .......................... A61K 51/0482; C07D 243/08
See application file for complete search history.

(56) References Cited

U.S. PATENT DOCUMENTS 7,186,400 B2 * 3/2007 Giovenzana ......... A61K 49/101
534/10

FOREIGN PATENT DOCUMENTS

WO 2014/198478 12/2014

OTHER PUBLICATIONS

Romba et al., Eur. J. Inorg. Chem. 2006, p. 314-328. (Year: 2006).*
Snodin et al., Chem. Eur. J., 1999, 5(9), p. 2554-25656. (Year: 1999).*
Liu et al., Inorg. Chem., 1993, 32, p. 2773-2778. (Year: 1993).*
Teresa M. Jones-Wi Lson et al: "New hydroxybenzyl and hydroxypyridylmethyl substituted triazacyclononane ligands for use with gallium(III) and indium(III)", Nuclear Medicine and Biology, vol. 22. No. 7., pp. 859-868, Oct. 1, 1995.

* cited by examiner

*Primary Examiner* — Michael G. Hartley
*Assistant Examiner* — Leah H Schlientz
(74) *Attorney, Agent, or Firm* — JMB Davis Ben-David

(57) ABSTRACT

The invention relates to compounds according to the general formula (I) or a pharmaceutically acceptable salt of an inorganic or organic acid, a hydrate, a stereoisomer or a solvate thereof, $R^1$, $R^2$, $R^3$, $R^4$, $R^5$, $R^6$, $R^7$, $R^8$, $R^9$, $R^{10}$, $R^{11}$ and $R^{12}$ being selected independently of one another from hydrogen and alkoxy. The compounds of formula (I) as ligands are suitable for the production of radioactively labelled $^{68}$Ga, $^{64}$Cu, $^{67}$Ga, $^{111}$In or $^{99m}$Tc complexes. The invention further relates to a method for producing the compounds of formula (I) and the radioactively labelled complexes and to the use of the radioactively labelled complexes in imaging methods, such as PET/CT, in particular of the liver.

21 Claims, No Drawings

DAZA CHELATORS AS LIGANDS IN LIVER IMAGING

CROSS-REFERENCE TO RELATED APPLICATIONS

This is the U.S. National Stage of International Patent Application No. PCT/EP2018/084107 filed on Dec. 10, 2018, which in turn claims the benefit of German Patent Application No. 102017129405.8 filed on Dec. 11, 2017.

FIELD OF THE INVENTION

The invention relates to novel ligands in liver imaging with PET/CT and to a method for preparing these compounds. The invention also relates to the use of these ligands in liver imaging methods.

BACKGROUND TO THE INVENTION

Liver imaging is currently carried out mainly by contrast medium-enhanced CT and MRI (the latter often with liver-specific contrast medium) and scintigraphic imaging (SPECT). Various liver-specific MRI contrast media are known in the prior art. However, some of the known contrast media that have been clinically tested, for example Endorem®, or have been granted approval, for example Resovist®, have disadvantages including undesirable toxic effects. There are, moreover, various approaches to liver imaging with PET/CT[68] using Ga tracers, but all have disadvantages associated with them. Table 1 shows an overview of contrast media currently used in various imaging methods.

TABLE 1

Conventional contrast media and radiotracers for various imaging methods

| Method | Metal complex for molecular imaging | Disadvantages |
|---|---|---|
| MRI | Contrast medium Primovist [9-13] | Contraindications: Metal implants, claustrophobia; contrast medium toxicity, administration of large amounts of substance, intolerances or allergies |
| SPECT and SPECT/CT | $^{99m}$Tc-EHIDA[14] | Lower spatial and temporal resolution than PET/CT or MRI |
| PET and PET/CT | Visualization of the asialoglycoprotein transporter on hepatocytes with 68Ga tracers: | |
| | $^{68}$Ga-DTPA-GSA[15] | Rapid decomposition of the complex in vivo limits its applicability |
| | $^{68}$Ga-NOTA-GSA[16] | Purification of the product through cartridges not possible, use of guaranteed $^{68}$Ge-free eluates or prepurification of the eluate necessary |
| | $^{68}$Ga-NOTA-LSA[17] | Differentiation between $^{68}$Ga-transferrin and $^{68}$Ga-NOTA-LSA difficult, because $^{68}$Ga-NOTA-LSA likewise has a peptide-like structure on account of the LSA-separation by LC methods (radio-HPLC or radio-TLC) not possible! This also means, for example, that identification of isomers (by radio-HPLC) of tracers is not possible. |
| | $^{68}$Ga-NODAGA-RGD[18] | No enhanced uptake in HCC by comparison with the adjoining liver tissue, therefore no tumor imaging possible; Accumulation in bladder, kidney and other organs, consequent radiation exposure in adjoining, untargeted organs, poorer image quality due to accumulation in non-hepatobiliary tissue, diagnosis more difficult |
| PET and PET/CT | $^{68}$Ga-oxine in lipiodol[19] | Laborious and time-consuming synthesis of $^{68}$Ga-oxine (including: extraction in chloroform), leakage of $^{68}$Ga-oxine from the lipiodol, e.g. due to instability of the complex. |
| PET/MR | $^{68}$Ga-siloxane-DO3A-labeled iron nanoparticles[20] | Accumulation in the liver and spleen, and to a limited degree through embolization in the lungs too, resulting in radiation exposure of adjoining untargeted organs |

The described disadvantages mean that Primovist® is currently the sole liver-specific contrast medium that is commercially available and used. However, the costs for one patient dose are high. Additional costs arise from delayed imaging and the accordingly long period of use of the MRI scanner that is necessary. In addition, the contraindications associated with Primovist® mean that CT or MRI examinations that are actually indicated often cannot be carried out or are possible only after premedication. Moreover, numerous MRI examinations cannot be carried out in patients with implanted pacemakers and in patients who suffer from claustrophobia.

WO2014198478 A2 discloses bifunctional chelators based on the 1,4-diazepan-6-amine (DAZA) framework for non-invasive molecular imaging. The 2-hydroxybenzyl-substituted DAZA unit acts as a coordinating unit for $^{68}$Ga. However, the properties for specific biodistribution are achieved only very laboriously via particular substituents of the DAZA, to which a coupling unit and a targeting unit are attached.

Also known from the literature are so-called DATA chelators, examples of which include the ligands AAZTA and AAZ3A[24,25]. These are characterized by functionalization of the nitrogen atoms with acetic acid groups or with long-chain carboxylic acids (for example glutaric acid[26]), methyl groups, phosphonates or ring systems capable of coordination.[24,25,27-41] Here, the 1,4-diazepan-6-amine is often extended at the C1 carbon atom of the DAZA ring by a functional group (for example methyl, phenyl [42] or linkers for bifunctional structures[30,31,33]). Moreover, a wide range of aminophenolate-containing ligands are known, which can be classified through the attachment of ortho-hydroxybenzyl units (for example in the form of phenolates or catecholates) both to open-chain structures (for example HBED[43] and TREN derivatives[44-48]) and to macrocycles such as cycles[49-54] and TACN[55-59]. These have for the most part already been investigated as ligands for $^{68}$Ga.[43,55,60]

DESCRIPTION OF THE INVENTION

The object of the invention was to provide ligands for liver imaging with PET/CT that have improved properties compared to the ligands known from the prior art and that can be prepared particularly easily and with little work involved.

This object is achieved by providing compounds corresponding to the general formula I:

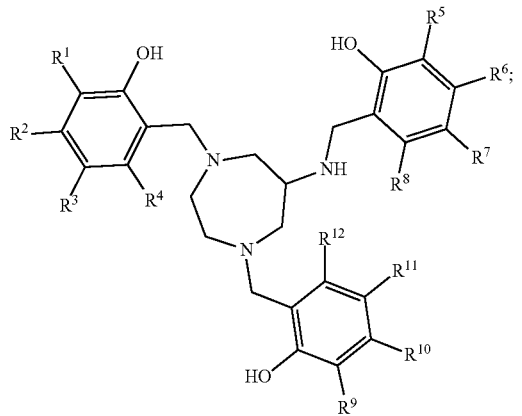

(I)

or a pharmaceutically acceptable salt of an inorganic or organic acid, of a hydrate, of a stereoisomer or of a solvate, including a radiolabeled complex thereof, where $R^1$, $R^2$, $R^3$, $R^4$, $R^5$, $R^6$, $R^7$, $R^8$, $R^9$, $R^{10}$, $R^{11}$, and $R^{12}$ are independently selected from hydrogen and alkoxy.

In the description and in the claims, the term "alkoxy", unless specifically limited, denotes a $C_{1-12}$ alkoxy group, preferably a $C_{1-8}$ alkoxy group, for example a $C_{1-6}$ alkoxy group or a $C_{1-4}$ alkoxy group. Alkoxy groups may be unbranched or branched. Examples of alkoxy groups include methoxy, ethoxy, propoxy (for example n-propoxy), butoxy (for example n-butoxy), pentoxy (for example n-pentoxy), hexoxy (for example n-hexoxy), heptoxy (e.g. n-heptoxy) and octoxy (for example n-octoxy).

"Substituted by hydrogen" in the context of the invention means "substituted by H".

The compounds of the formula I are particularly suitable ligands for the formation of radiolabeled complexes. In a preferred embodiment, the invention provides radiolabeled complexes that consist of a compound of the formula I and a radioisotope selected from the group comprising $^{68}$Ga, $^{64}$Cu, $^{67}$Ga, $^{111}$In, and $^{99m}$Tc. In a preferred embodiment, the radiolabeled complex is a complex corresponding to the general formula II:

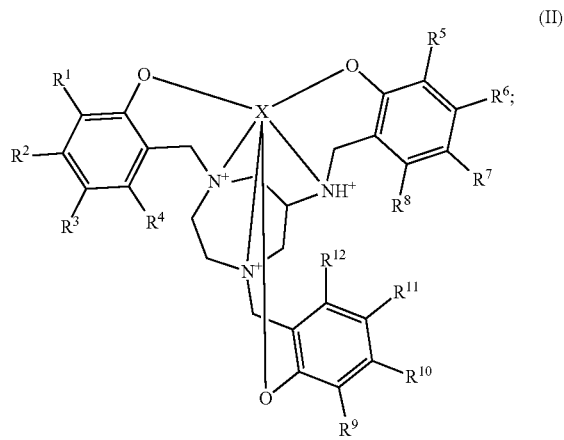

(II)

or of a pharmaceutically acceptable salt of an inorganic or organic acid, of a hydrate, of a stereoisomer or of a solvate thereof, where $R^1$, $R^2$, $R^3$, $R^4$, $R^5$, $R^6$, $R^7$, $R^8$, $R^9$, $R^{10}$, $R^{11}$, and $R^{12}$ are as defined for the compound of the formula 1 and where X is selected from $^{68}$Ga, $^{67}$Ga, and $^{111}$In.

In accordance with the invention, it is preferable when each of the hydroxybenzyl groups in the compounds of the formula I or formula II has an alkoxy group as a substituent and the other three substituents are hydrogen. Thus, in a preferred embodiment of the invention:
one of the substituents $R^1$, $R^2$, $R^3$, and $R^4$ is alkoxy and the other three substituents are hydrogen; and
one of the substituents $R^5$, $R^6$, $R^7$, and $R^8$ is alkoxy and the other three substituents are hydrogen; and
one of the substituents $R^9$, $R^{10}$, $R^{11}$, and $R^{12}$ is alkoxy and the other three substituents are hydrogen.

In a further preferred embodiment, the alkoxy groups in each of the hydroxybenzyl groups in the compounds of the formula I or of the formula II are all alkoxy-substituted either at the ortho, meta or para position.

Particularly preferred according to the invention are therefore compounds corresponding to formula I or formula II, where
$R^1$ is alkoxy and $R^2$, $R^3$, and $R^4$ are hydrogen; and
$R^5$ is alkoxy and $R^6$, $R^7$, and $R^8$ are hydrogen; and
$R^9$ is alkoxy and $R^{10}$, $R^{11}$, and $R^{12}$ are hydrogen;
or
$R^2$ is alkoxy and $R^1$, $R^3$, and $R^4$ are hydrogen; and
$R^6$ is alkoxy and $R^5$, $R^7$, and $R^8$ are hydrogen; and
$R^{10}$ is alkoxy and $R^9$, $R^{11}$, and $R^{12}$ are hydrogen;
or
$R^3$ is alkoxy and $R^1$, $R^2$, and $R^4$ are hydrogen; and
$R^7$ is alkoxy and $R^5$, $R^6$, and $R^8$ are hydrogen; and
$R^{11}$ is alkoxy and $R^9$, $R^{10}$, and $R^{12}$ are hydrogen;
or
$R^4$ is alkoxy and $R^1$, $R^2$, and $R^3$ are hydrogen; and
$R^8$ is alkoxy and $R^5$, $R^6$, and $R^7$ are hydrogen; and $R^{12}$ is alkoxy and $R^9$, $R^{10}$, and $R^{11}$ are hydrogen.

It is very particularly preferable when the alkoxy groups in each of the hydroxybenzyl groups in the compounds of the formula I or formula II are all alkoxy-substituted at the meta position. Thus, in a very particularly preferred embodiment of the invention:

$R^2$ is alkoxy and $R^1$, $R^3$, and $R^4$ are hydrogen; and
$R^6$ is alkoxy and $R^5$, $R^7$, and $R^8$ are hydrogen; and
$R^{10}$ is alkoxy and $R^9$, $R^{11}$, and $R^{12}$ are hydrogen;

This structural modification to the three phenolate groups of the modified DAZA makes it possible to achieve the desired specific biodistribution without there being a need for a targeting unit to be attached. The reason for this is that the desired high liver specificity is achieved in a simple manner via the coordinating alkoxyhydroxybenzyl groups through their additional alkoxy substituents.

In the compounds of the formula I and II according to the invention, aside from the three hydroxybenzyl groups, DAZA is substituted exclusively by hydrogen. In contrast to this, the DAZA framework of the compounds disclosed in WO2014198478 A2 has further substituents other than hydrogen. This means that the specific liver distribution for the substances disclosed in WO2014198478 A2 cannot be guaranteed. The compounds of the formula I and II according to the invention are additionally particularly advantageous, since the substances are obtainable via a simple synthetic route starting from the DAZA. Additional synthetic steps to attach targeting units are not necessary.

The absence of substituents other than H on the DAZA means that no disadvantages as regards the coordination ability of $^{68}$Ga, $^{64}$Cu, $^{67}$Ga, $^{111}$In, and $^{99m}$Tc are observed in the compounds of the formula I according to the invention—the complexes form in less than 10 min at room temperature, preferably at elevated temperature, and are stable in vivo.

When $R^2$, $R^6$, and $R^{10}$ are substituted by alkoxy, the alkoxy substituent is, for example, independently —O—$C_{1-12}$ alkyl, preferably —O—$C_{1-8}$ alkyl, more preferably —O—$C_{1-6}$ alkyl or —O—$C_{1-4}$ alkyl, wherein the alkyl radical may be unbranched or branched.

In a further preferred embodiment, the alkoxy substituents are independently selected from methoxy, ethoxy, propoxy, butoxy, pentoxy, heptoxy, hexoxy, and octoxy. In particularly preferred compounds of the formula I and of the formula II, $R^2$, $R^6$, and $R^{10}$ are independently substituted by methoxy, ethoxy, propoxy, butoxy, pentoxy, heptoxy, hexoxy or octoxy, and $R^1$, $R^3$, $R^4$, $R^5$, $R^7$, $R^8$, $R^9$, $R^{11}$, and $R^{12}$ are substituted by hydrogen.

An advantageous liver distribution was achieved with compounds of the formula I and of the formula II when the hydroxybenzyl groups are each substituted by the same alkoxy group, preferably when $R^2$, $R^6$, and $R^{10}$ are substituted by the same alkoxy group. In a preferred embodiment, the hydroxybenzyl groups are each substituted by ethoxy, particularly preferably at positions $R^2$, $R^6$, and $R^{10}$. In a likewise preferred embodiment, the hydroxybenzyl groups are each substituted by methoxy, particularly preferably at positions $R^2$, $R^6$, and $R^{10}$. The other substituents of the hydroxybenzyl groups are each substituted by hydrogen, particularly preferably the positions $R^1$, $R^3$, $R^4$, $R^5$, $R^7$, $R^8$, $R^9$, $R^{11}$, and $R^{12}$.

The purpose of the invention was that it should extend the principle of "liver imaging by injection of hepatotropic metal complex solutions" from paramagnetic metals (Gd (III)-MRI) and radioactive metal isotopes as gamma emitters ($^{99m}$Tc-SPECT) to metal complexes containing gallium(III) or Cu(III), specifically the radioactive $^{68}$Ga isotope and the radioactive $^{64}$Cu isotope, which are used as positron emitters in PET/CT imaging. The central challenge was the synthesis of a ligand suitable for labeling with $^{68}$Ga, $^{64}$Cu, $^{67}$Ga, $^{111}$In or preferably with $^{68}$Ga or $^{64}$Cu, that was at the same time liver-specific. The ligands EOB-DTPA and EHIDA employed in the routinely used metal complex solutions "Primovist®" (Gd-EOB-DTPA) and "$^{99m}$Tc-EHIDA" do not form sufficiently stable $^{68}$Ga complexes[1,21]. Instead, the compounds show rapid disintegration under physiological conditions, which is primarily characterized by demetalation (e.g. by the blood protein apo-transferrin).[22] The $^{68}$Ga ion thereby released in vivo (e.g. in the form of colloids, tetrahydroxogallate or in protein-bound form) exhibits a nonspecific distribution in the blood pool and insufficient accumulation of the radioactive component in the liver, which hinders its imaging. It is therefore essential for complexes to have high stability in order for them to be usable. By definition, it needs to be possible for a correspondingly suitable ligand for $^{68}$Ga and $^{64}$Cu to be synthesized as efficiently, and in as few steps, as possible and starting from available starting materials. This would also allow easy modification of the ligand framework, for example in respect of functional, lipophilic groups (chain length or positioning of the alkoxy groups on the benzyl ring), and thus optimization of the tracer structure and of the in-vivo distribution thereof.

The compounds of the formula I according to the invention are generally suitable for labeling with $^{68}$Ga, $_{64}$Cu, $_{67}$Ga, $^{111}$In or $^{99m}$Tc, but particularly suited for labeling with $^{68}$Ga. Unlike with the above-mentioned and known ligands EOB-DTPA and EHIDA, the $^{68}$Ga complexes of the compounds of the formula II show no demetalation or decomposition in vivo. The ligands are stable and can be stored as precursors for labeling with $^{68}$Ga or $^{64}$Cu. Because of the small amounts of substance administered, no adverse toxicological effects are to be expected. The labeling of $^{68}$Ga, $^{64}$Cu, $^{67}$Ga, $^{111}$In or $^{99m}$Tc for the synthesis of the tracer is carried out according to standard radiopharmaceutical methods. Access to $^{68}$Ge/$^{68}$Ga generators, which are known to those skilled in the art, ensures the practically unrestricted availability of, for example, the radionuclide $^{68}$Ga.

In a particularly preferred embodiment of the invention, the compound of the formula I is selected from tris-N,N', N"(4-ethoxy-2-hydroxybenzyl)-1,4-diazepan-6-amine (TEOHB-DAZA) and tris-N,N',N"(4-methoxy-2-hydroxybenzyl)-1,4-diazepan-6-amine (TMeOHB-DAZA) and the corresponding radiolabeled complexes of the formula II are selected from:

| Example No. | Compound | Abbreviation |
| --- | --- | --- |
| 1 | $^{68}$Ga[tris-N,N',N"(4-ethoxy-2-hydroxybenzyl)-1,4-diazepan-6-amine] | $^{68}$Ga-[TEOHB-DAZA] |
| 2 | $^{68}$Ga[tris-N,N',N"(4-methoxy-2-hydroxybenzyl)-1,4-diazepan-6-amine] | $^{68}$Ga-[TMeOHB-DAZA] |
| 3 | $^{64}$Cu[tris-N,N',N"(4-ethoxy-2-hydroxybenzyl)-1,4-diazepan-6-amine] | $^{64}$Cu-[TEOHB-DAZA] |
| 4 | $^{64}$Cu[tris-N,N',N"(4-methoxy-2-hydroxybenzyl)-1,4-diazepan-6-amine] | $^{64}$Cu-[TMeOHB-DAZA] |
| 5 | $^{67}$Ga[tris-N,N',N"(4-ethoxy-2-hydroxybenzyl)-1,4-diazepan-6-amine] | $^{67}$Ga-[TEOHB-DAZA] |
| 6 | $^{67}$Ga[tris-N,N',N"(4-methoxy-2-hydroxybenzyl)-1,4-diazepan-6-amine] | $^{67}$Ga-[TMeOHB-DAZA] |
| 7 | $^{111}$In[tris-N,N',N"(4-ethoxy-2-hydroxybenzyl)-1,4-diazepan-6-amine] | $^{111}$In-[TEOHB-DAZA] |
| 8 | $^{111}$In[tris-N,N',N"(4-methoxy-2-hydroxybenzyl)-1,4-diazepan-6-amine] | $^{111}$In-[TMeOHB-DAZA] |

-continued

| Example No. | Compound | Abbreviation |
|---|---|---|
| 9 | $^{99m}$Tc[tris-N,N',N''(4-ethoxy-2-hydroxybenzyl)-1,4-diazepan-6-amine] | $^{99m}$Tc-[TEOHB-DAZA] |
| 10 | $^{99m}$Tc[tris-N,N',N''(4-methoxy-2-hydroxybenzyl)-1,4-diazepan-6-amine] | $^{99m}$Tc-[TMeOHB-DAZA] |

The invention further provides the following compounds:

| Example No. | Compound |
|---|---|
| 11 | $^{68}$Ga[tris-N,N',N''(3-ethoxy-2-hydroxybenzyl)-1,4-diazepan-6-amine] |
| 12 | $^{68}$Ga[tris-N,N',N''(5-ethoxy-2-hydroxybenzyl)-1,4-diazepan-6-amine] |
| 13 | $^{68}$Ga[tris-N,N',N''(6-ethoxy-2-hydroxybenzyl)-1,4-diazepan-6-amine] |
| 14 | $^{68}$Ga[tris-N,N',N''(3-methoxy-2-hydroxybenzyl)-1,4-diazepan-6-amine] |
| 15 | $^{68}$Ga[tris-N,N',N''(5-methoxy-2-hydroxybenzyl)-1,4-diazepan-6-amine] |
| 16 | $^{68}$Ga[tris-N,N',N''(6-methoxy-2-hydroxybenzyl)-1,4-diazepan-6-amine] |
| 17 | $^{64}$Cu[tris-N,N',N''(3-ethoxy-2-hydroxybenzyl)-1,4-diazepan-6-amine] |
| 18 | $^{64}$Cu[tris-N,N',N''(5-ethoxy-2-hydroxybenzyl)-1,4-diazepan-6-amine] |
| 19 | $^{64}$Cu[tris-N,N',N''(6-ethoxy-2-hydroxybenzyl)-1,4-diazepan-6-amine] |
| 20 | $^{64}$Cu[tris-N,N',N''(3-methoxy-2-hydroxybenzyl)-1,4-diazepan-6-amine] |
| 21 | $^{64}$Cu[tris-N,N',N''(5-methoxy-2-hydroxybenzyl)-1,4-diazepan-6-amine] |
| 22 | $^{64}$Cu[tris-N,N',N''(6-methoxy-2-hydroxybenzyl)-1,4-diazepan-6-amine] |
| 23 | $^{67}$Ga[tris-N,N',N''(3-ethoxy-2-hydroxybenzyl)-1,4-diazepan-6-amine] |
| 24 | $^{67}$Ga[tris-N,N',N''(5-ethoxy-2-hydroxybenzyl)-1,4-diazepan-6-amine] |
| 25 | $^{67}$Ga[tris-N,N',N''(6-ethoxy-2-hydroxybenzyl)-1,4-diazepan-6-amine] |
| 26 | $^{67}$Ga[tris-N,N',N''(3-methoxy-2-hydroxybenzyl)-1,4-diazepan-6-amine] |
| 27 | $^{67}$Ga[tris-N,N',N''(5-methoxy-2-hydroxybenzyl)-1,4-diazepan-6-amine] |
| 28 | $^{67}$Ga[tris-N,N',N''(6-methoxy-2-hydroxybenzyl)-1,4-diazepan-6-amine] |
| 29 | $^{111}$In[tris-N,N',N''(3-ethoxy-2-hydroxybenzyl)-1,4-diazepan-6-amine] |
| 30 | $^{111}$In[tris-N,N',N''(5-ethoxy-2-hydroxybenzyl)-1,4-diazepan-6-amine] |
| 31 | $^{111}$In[tris-N,N',N''(6-ethoxy-2-hydroxybenzyl)-1,4-diazepan-6-amine] |
| 32 | $^{111}$In[tris-N,N',N''(3-methoxy-2-hydroxybenzyl)-1,4-diazepan-6-amine] |
| 33 | $^{111}$In[tris-N,N',N''(5-methoxy-2-hydroxybenzyl)-1,4-diazepan-6-amine] |
| 34 | $^{111}$In[tris-N,N',N''(6-methoxy-2-hydroxybenzyl)-1,4-diazepan-6-amine] |
| 35 | $^{99m}$Tc[tris-N,N',N''(3-ethoxy-2-hydroxybenzyl)-1,4-diazepan-6-amine] |
| 36 | $^{99m}$Tc[tris-N,N',N''(5-ethoxy-2-hydroxybenzyl)-1,4-diazepan-6-amine] |
| 37 | $^{99m}$Tc[tris-N,N',N''(6-ethoxy-2-hydroxybenzyl)-1,4-diazepan-6-amine] |
| 38 | $^{99m}$Tc[tris-N,N',N''(3-methoxy-2-hydroxybenzyl)-1,4-diazepan-6-amine] |
| 39 | $^{99m}$Tc[tris-N,N',N''(5-methoxy-2-hydroxybenzyl)-1,4-diazepan-6-amine] |
| 40 | $^{99m}$Tc[tris-N,N',N''(6-methoxy-2-hydroxybenzyl)-1,4-diazepan-6-amine] |

The accumulation in the liver of the compounds according to the invention can be examined in a so-called ovo test, i.e. in vivo in an incubated ostrich egg. The administration of $^{68}$Ga-[TEOHB-DAZA] showed almost exclusive accumulation in the liver in the embryonated ostrich egg.

A further advantage of the compounds according to the invention is the easy obtainability of the ligands TEOHB-DAZA and TMeOHB-DAZA starting from DAZA via an efficient one-pot synthesis (see below) in which only NaBH4 as reducing agent is used. The starting material DAZA is synthesized according to a literature procedure.[23]

In a further aspect, the invention provides pharmaceutical compositions comprising a compound of the formula I or of the formula II or a pharmaceutically acceptable salt of an inorganic or organic acid, a hydrate, a stereoisomer or a solvate of such a compound. The pharmaceutical composition preferably comprises at least one physiologically tolerated vehicle, diluent, adjuvant and/or excipient.

As used in the description of the invention and in the claims, the terms "inorganic acid" and "organic acid" refer to mineral acids including, but not limited to, acids such as carbonic acid, nitric acid, hydrochloric acid, hydrobromic acid, hydroiodic acid, phosphoric acid, perchloric acid or sulfuric acid or the acidic salts thereof, such as potassium hydrogen sulfate, or suitable organic acids, which include acids such as aliphatic, cycloaliphatic, aromatic, araliphatic acids, heterocyclic carboxylic acids, and sulfonic acids. Examples thereof are formic acid, acetic acid, trifluoroacetic acid, propionic acid, succinic acid, glycolic acid, gluconic acid, lactic acid, malic acid, fumaric acid, pyruvic acid, benzoic acid, anthranilic acid, methanesulfonic acid, fumaric acid, salicylic acid, phenylacetic acid, mandelic acid, embonic acid, methanesulfonic acid. Ethanesulfonic acid, benzenesulfonic acid, pantothenic acid, toluenesulfonic acid, trifluoromethanesulfonic acid, 1,1,2,2,3,3,4,4,4-nonafluorobutane-1-sulfonic acid or sulfanilic acid.

In a further aspect of the invention, a radiopharmaceutical composition is provided that comprises a compound of the formula II or a pharmaceutically acceptable salt of an inorganic or organic acid, a hydrate, a stereoisomer or a solvate of such a compound.

The radiopharmaceutical composition preferably comprises at least one physiologically tolerated vehicle, diluent, adjuvant and/or excipient.

The compounds according to the present invention, preferably the radiolabeled compounds corresponding to formula II, that are provided by the invention may be intravenously contained as a pharmaceutical composition for intravenous injection in a pharmaceutically acceptable vehicle, for example in a conventional medium such as an aqueous saline medium or in blood plasma medium or serum. Such a medium may also contain conventional pharmaceutical substances such as pharmaceutically acceptable salts for adjusting the osmotic pressure, buffers, preservatives and the like. Preferred media include physiological saline and human serum. A particularly preferred medium is PBS-buffered saline.

Other suitable pharmaceutically acceptable vehicles are known to those skilled in the art, for example from Remington's Practice of Pharmacy, 13th edition and J. of Pharmaceutical Science & Technology, vol. 52, No. 5, September-October, pp. 238-311.

In accordance with the invention, the radiolabeled compounds of the general formula II are administered either as a neutral composition or as a salt having a pharmaceutically acceptable counterion as described above, in a single injectable dose unit. After radiolabeling, any of the usual vehicles known to those skilled in the art, such as sterile saline or plasma, preferably PBS-buffered saline, may be used to prepare the injectable solution for diagnostic imaging of various organs, preferably the liver. The unit dose to be administered for a diagnostic agent typically has a radioactivity from about 3.7 MBq to about 37 GBq. In accordance with the invention, the pharmaceutical/radiopharmaceutical compositions have a radioactivity of at least 50 MBq, These are particularly suitable for liver imaging methods, The volume of solution to be injected in the unit dose is in the range from about 0.01 ml to about 30 ml. For diagnostic purposes after intravenous administration, imaging of the organ or of the disease may take place in vivo within a few minutes. However, imaging may, if desired, take place hours or even longer after injection into patients. In most cases, a sufficient amount of the administered activity will accumulate in the area to be imaged within about 30 min, allowing images to be recorded in imaging methods. Any conventional diagnostic imaging method may be employed in accordance with this invention. Preference is given to using the $^{68}$Ga and $^{64}$Cu complexes of the formula II in imaging by PET/CT. PET/CT imaging with compounds of the formula II according to the invention is preferably carried out for 0.5 h to 2 h per injection ("normal" phase and "late/biliary" phase) or dynamically in list mode. It is likewise possible to record the early phase (arterial flooding) through administration directly in the PET/CT scanner (so-called "early-dynamic PET").

Another advantage of the pharmaceutical/radiopharmaceutical composition according to the invention is high stability. The compositions according to the invention have a stability of at least 98% for at least 4 hours in (human serum or PBS-buffered saline). Further preference is given to using $^{67}$Ga, $^{111}$In or $^{99m}$Tc complexes of the formula II in imaging by SPECT and SPECT/CT.

The compounds of the formula II show liver-specific accumulation and are excreted via the intestine and/or the gallbladder.

In a further aspect of the invention, a method for preparing a compound of the general formula I is provided. In a preferred embodiment, the preparation of a compound of the general formula I comprises the steps of:

a) synthesizing a compound of the formula III

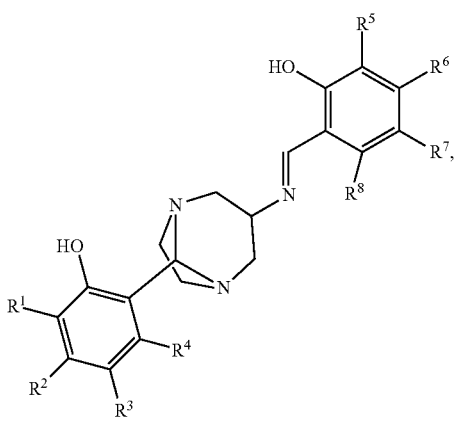

where R1, $_R$2, $_R$3, R4, R5, Rs, R$^7$, and R$^8$ are defined as described above;

through reaction of a compound of the formula IV

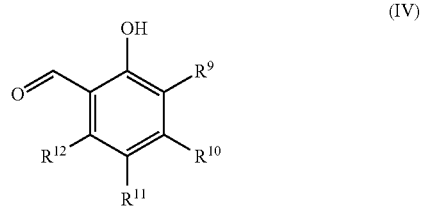

where R$^9$, R$^{10}$, R$^{11}$, and R$^{12}$ are defined as described above, with a compound of the formula (V):

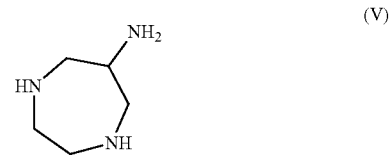

in the presence of a suitable solvent, such as methanol; and b) reacting the compound of the formula III under reducing conditions with a suitable reducing agent, such as NaBH$_4$, in the presence of a suitable solvent.

When alkoxy in the compound of the formula I is ethoxy, preference is given to using methanol as the solvent in step b) of the preparation process. When alkoxy in the compound of the formula I is methoxy, preference is given to using a mixture of methanol and chloroform, preferably in a ratio of 1:1, as solvent in step b) of the preparation process.

The synthesis of TEOHB-DAZA and TMeOHB-DAZA proceeds via a bicyclic precursor of the formula III containing an N,N'-bridging element provided by an aminal linkage:

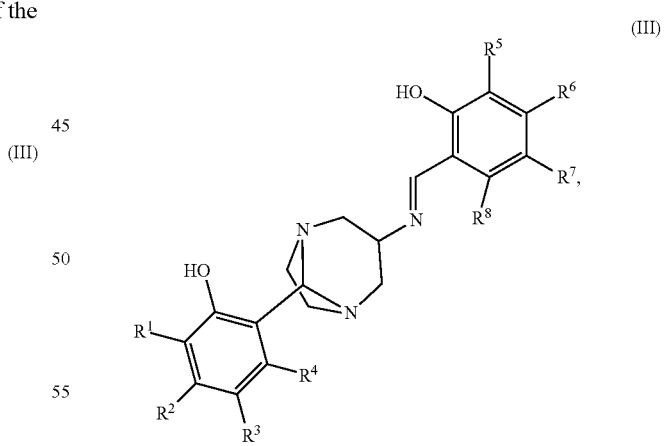

It was surprisingly found that in step b), under reducing conditions, the triply alkylated product TEOHB-DAZA or TMeOHB-DAZA can be synthesized in very good yields from the azacycle functionalized with two 4-alkoxy-2-hydroxybenzyl units (one bonded in the form of an aminal and one in the form of an imine). In a preferred embodiment of the invention, a C═O or C═N component is inserted into one of the two C—N bonds of the aminal with subsequent reduction, for example by the hydride reagent NaBH$_4$.

The reductive cleavage of aminals to the corresponding amines is known in the literature;[61-64] in the known processes, cleavage always occurs between one of the two nitrogen atoms N and the carbon bridge, with the result that, after reduction of one of the nitrogen atoms N', the functional radical of the reduced aminal bears as corresponding alkyl substituents, whereas the second nitrogen atom N adds a proton and is present as $R_2NH$. However, there have been no reports to date of a bis-N,N'-alkylated amine structure being formed from an N,N'-bridged aminal structure under reducing conditions. However, this is exactly what happens in the method according to the invention. The resulting compounds of the formula I were unambiguously demonstrated/identified by X-ray structural analysis.

This specific reaction makes it possible, in a one-pot synthesis starting with the unprotected 1,4-diazepan-6-amine, to selectively alkylate, through the carbonyl component, each of the three nitrogen atoms in the compound of the formula I with an alkyl radical, even though these comprise two secondary amino groups and one that is primary. According to the existing prior art, the alkylation of secondary amines through condensation with aldehydes and other carbonyl components in particular takes place only through direct reductive amination in the presence of modified, milder reducing agents such as $NaBH(OAc)_3$ or $NaBH_3CN$.[65] Furthermore, attempts at alkylating such an azacycle, especially when selectivity is desired, for example the single alkylation of the primary amino group, often results in mixtures of products, particularly in the reaction with routinely employed alkyl bromides, or necessitate the use of protective groups.[25,34,66,67]

In the reaction according to the invention, the tris-N,N',N''-alkylated 1,4-diazepan-6-amines TEOHB-DAZA and TMeOHB-DAZA are formed in very high yields of 80-90% (calculated based on the molar ratio of 4-alkoxy-2-hydroxybenzyl groups in the precursor (=2 units) and in the product (=3 units)). Through this reaction, the inventors have succeeded in establishing a new reaction pathway for the efficient, protective group-free, single alkylation of all three nitrogen atoms in 1,4-diazepan-6-amine (DAZA) starting from the corresponding carbonyl component. It was also found that the structurally related TOHB-DAZA (tris-N,N',N''-(2-hydroxybenzyl)-1,4-diazepan-6-amine)) and TEOB-DAZA (tris-N,N',N''-(4-ethoxybenzyl)-1,4-diazepan-6-amine) cannot be isolated by the same method. In the reduction of the corresponding bridged aminals (III), there is increased formation of product mixtures of mono-, di-, and trialkylated DAZA and (especially in the case of TEOB-DAZA) aldehyde (IV), which are difficult to separate from one another. Selective precipitation of the trialkylated products from methanol, as for TEOHB-DAZA and TMeOHB-DAZA, does not occur.

In a further aspect, the invention relates to the use of a compound of the formula I as a ligand for preparing a $^{68}Ga$ or $^{64}Cu$ complex corresponding to the formula II. A method for preparing a compound of the formula II from a compound of the formula I is also provided.

In this method according to the invention, a compound of the formula I is treated with a $^{68}Ga$-containing solution or a $^{64}Cu$-containing solution at room temperature or higher. The treatment is preferably carried out at 50° C. or higher, more preferably at 60° C., 70° C., 80° C., 90° C. or higher, particularly preferably at 100° C. The higher the temperature chosen, the shorter the reaction time until the formation of the radiolabeled complex, which is particularly advantageous for the performance of imaging methods, since the radiolabeled compounds of the formula II should not be synthesized until as close as possible to administration to the patient and—if needed at short notice—can be provided within a few minutes, for example within 5 minutes, when the reaction is carried out at 100° C.

The yields of the compounds of the formula II that can be achieved are also pH-dependent. If $^{68}Ga$ is to be incorporated into a ligand of the formula I, the treatment of the ligand of the formula I with a $^{68}Ga$-containing solution is preferably carried out at a pH of 5.0 or lower, more preferably in the range from 3.7 to 5.0, particularly preferably in the range from 4.0 to 4.5. If $^{64}Cu$ is to be incorporated into a ligand of the formula I, the treatment of the ligand of the formula I with a $^{64}Cu$-containing solution is preferably carried out at a pH of 4.0 or higher, more preferably in the range from 4.0 to 8.0, particularly preferably in the range from 6.0 to 7.0.

The invention also provides a kit for preparing a radiopharmaceutical preparation, wherein the kit comprises a sealed ampoule containing a predetermined amount of a ligand of the invention corresponding to the formula I or a compound of the formula II and optionally instructions for using the components of the kit. The present invention also provides a kit for the imaging of diseases.

In a further aspect, the invention provides the compounds of the formula II or (radio)pharmaceutical compositions comprising a compound of the formula II for use in diagnostic methods such as PET/CT imaging.

The invention further relates to the use of compounds of the formula II for preparing a (radio)pharmaceutical composition for diagnostic purposes, for example for imaging methods such as PET/CT. In particular, the compounds of this invention are useful for imaging of liver diseases including, but not limited to, chronic diseases and tumors of the liver. The compounds of the formula II allow, for example, the imaging of liver diseases selected from liver inflammation (hepatitis), liver cirrhosis (shrunken liver), fatty liver, autoimmune liver diseases such as autoimmune hepatitis (AIH), primarily sclerosing cholangitis (PSC) and primarily biliary cirrhosis (PBC), and iron storage disease (hemochromatosis).

The compounds of the formula II allow imaging of all primary and secondary tumors of the liver and bile ducts, for example hemangioma, hepatocellular adenoma, focal nodular hyperplasia (FNH), nodular regenerative hyperplasia (NRH), cholangioadenoma; hepatocellular carcinoma, cholangiocarcinoma, cystadenocarcinoma, angiosarcoma and hepatoblastoma, metastases of other tumors such as colorectal carcinoma; appendiceal carcinoids; mammary carcinoma, ovarian carcinoma, lung carcinoma, renal carcinoma, carcinoma of the prostate, and others.

In a further aspect, the invention relates to a treatment method or diagnostic method comprising the administration of a compound of the formula II or of a (radio)pharmaceutical composition comprising a compound of the formula II to a subject in a therapeutically active amount or in an amount sufficient for the performance of a diagnostic method. The subject is, for example, an animal, preferably a mammal, or more preferably a human.

Preference according to the invention is given to using or administering a compound of the formula II or a (radio) pharmaceutical composition comprising a compound of the formula II for PET/CT imaging of the liver.

In a particularly preferred embodiment of the invention, a method for obtaining an image of the liver of an animal or a human is provided, wherein the method comprises the following steps:

(a) administering to an animal or human a pharmaceutical composition comprising a compound of the formula II as claimed in any of claim 2-9 or 11,
(b) carrying out a PET or a PET/CT scan of the treated animal or human;
(c) detecting a measurable emission signal due to the compound of the formula II from the animal or human concerned; and
(d) generating an image from the detectable signal, thereby obtaining an image of the liver of the animal or human,

EXAMPLE EMBODIMENTS

1. Synthesis Description

The compounds of the formula I are synthesized as shown in scheme 1.

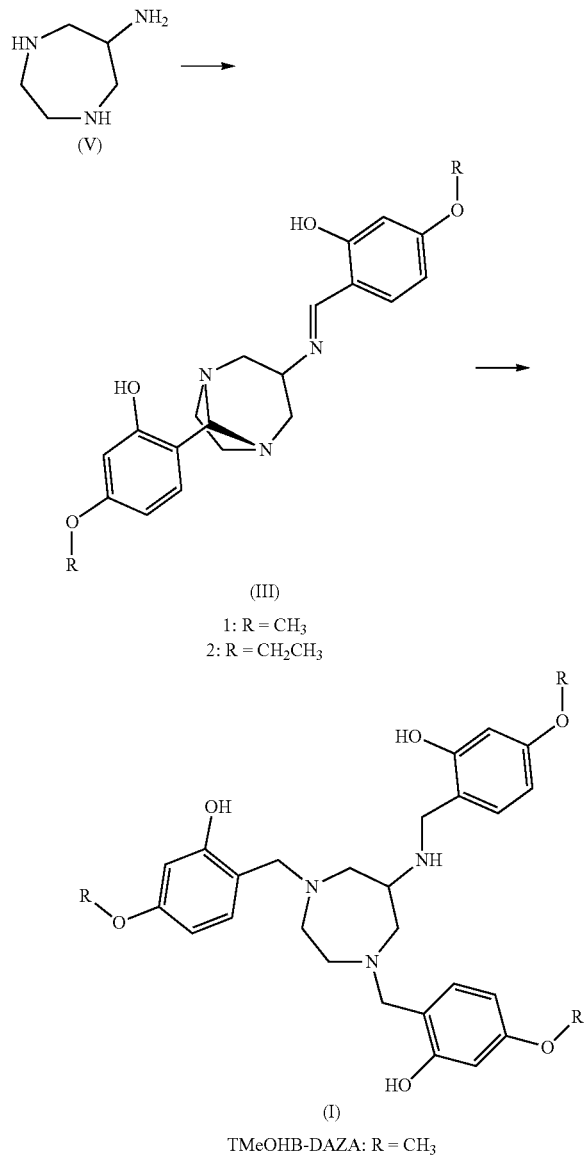

Scheme 1 Synthesis of the of the compounds of formula I.

1: R = CH₃
2: R = CH₂CH₃

TMeOHB-DAZA: R = CH₃
TEOHB-DAZA: R = CH₂CH₃

Synthesis of Precursors/Synthesis of 1

1,4-Diazepan-6-amine (65 mg, 0.57 mmol) and 4-methoxy-2-hydroxybenzaldehyde (172 mg, 1.13 mmol) in 15 ml methanol were mixed in a round-bottomed flask and the resulting yellow suspension was stirred for one hour at RT. The solid was filtered, washed with methanol, and dried under reduced pressure (205 mg, 0.54 mmol, 94%).

$^1$H-NMR (400.1 MHz, CDCl$_3$): δ=13.17 (s, broad, 1H), 11.85 (s, broad, 1H), 8.28 (s, 2H), 7.26-7.23 (m, 1H), 7.12 (d, $^3J_{H,H}$=8.4 Hz, 1H), 6.45-6.36 (m, HH), 5.21 (s, 1H), 3.81 (s, 3H), 3.76 (s, 3H), 3.71-3.64 (m, 1H), 3.37-2.90 (m, 8H).

$^{13}$C-NMR (100.6 MHz, CDCl$_3$): δ=165.0, 163.7, 163.5, 161.2, 158.5, 132.7, 128.0, 112.5, 106.9, 105.5, 101.8, 101.2, 87.4, 60.6, 59.1, 55.6, 55.3, 50.6.

MS (ESI pos., CH$_3$OH): m/z=383 ([M]$^+$, 100%).

EA [%] (C$_{21}$H$_{25}$N$_3$O$_4$): C 65.46 (65.78), H 6.72 (6.57), N 11.07 (10.96).

Synthesis of Precursors/Synthesis of 2

1,4-Diazepan-6-amine (30 mg, 0.26 mmol) and 4-ethoxy-2-hydroxybenzaldehyde (86 mg, 0.52 mmol) in 10 ml methanol were mixed in a round-bottomed flask and the resulting yellow suspension was stirred for one hour at RT. The solid was filtered, washed with methanol, and dried under reduced pressure (100 mg, 0.24 mmol, 94%).

$^1$H-NMR (400.1 MHz, CDCl$_3$): δ=13.16 (s, 1H), 8.27 (s, 2H), 7.24-7.22 (m, 2H), 7.12-7.09 (m, 2H), 6.45-6.41 (m, 2H), 6.38-6.35 (m, 4H), 5.60 (s), 5.21 (s, 1H), 4.07-3.96 (m, 4H), 3.72-3.64 (m, 1H), 3.49-2.90 (m, 8H), 1.43-1.36 (m, 6H).

$^{13}$C-NMR (62.9 MHz, CDCl$_3$): δ=165.0, 163.4, 163.0, 160.5, 158.5, 132.7, 128.0, 112.3, 107.4, 106.1, 102.3, 101.6, 87.4, 63.8, 63.5, 60.6, 59.1, 50.6, 15.0, 14.8.

MS (ESI pos., CH$_3$OH): m/z=434 ([M+Na]$^+$, 100%), 412 ([M+H]$^+$, 45%).

EA [%] (C$_{23}$H$_{29}$N$_3$O$_4$): C 66.90 (67.13), H 7.13 (7.10), N 10.26 (10.21).

Synthesis of the Ligand TMeOHB-DAZA

To a solution of 1 (200 mg, 0.52 mmol) in 10 ml of a 1:1 mixture of methanol and chloroform was added 71 mg (1.89 mmol) of NaBH4 in several portions, whereupon the solution decolorized. The reaction solution was stirred for one hour. The solvent was then removed under reduced pressure and the residue resuspended in methanol. The solid was filtered, washed with methanol, and then dried under reduced pressure (163 mg, 0.31 mmol, 60%).

$^1$H-NMR (400.1 MHz, CDCl$_3$): δ=10.45 (s, broad, 1H), 6.88 (d, $^3J_{H,H}$=8.1 Hz, 2H), 6.52 (d, $^3J_{H,H}$=8.4 Hz, 1H), 6.41-6.35 (m, 5H), 6.27 (dd, $^3J_{H,H}$=8.3 Hz, $^2J_{H,H}$=2.5 Hz, 1H), 3.82 (d, $^2J_{H,H}$=13.4 Hz, 2H), 3.75 (s, 6H), 3.74 (s, 3H), 3.67 (d, $^2J_{H,H}$=13.4 Hz, 2H), 3.37 (s, 2H), 2.98-2.72 (m, 9H).

$^{13}$C-NMR (100.6 MHz, CDCl$_3$): δ=161.1, 160.6, 159.2, 158.7, 129.7, 129.2, 114.4, 114.0, 105.9, 105.2, 102.1, 102.0, 62.5, 58.3, 57.9, 55.4, 54.7, 51.0, 49.4.

MS (ESI pos., CH$_3$OH): m/z=546 ([M+Na]$^+$, 45%), 524 ([M+H]$^+$, 100%).

EA [%] (C$_{32}$H$_{45}$N$_3$O$_7$·0.5MeOH): C 65.58 (65.66), H 7.07 (7.28), N 7.89 (7.79).

Synthesis of the Ligand TEOHB-DAZA

To a suspension of 2 (120 mg, 0.29 mmol) in 10 ml of methanol was added 22 mg (0.58 mmol) of NaBH$_4$ in several portions, whereupon the yellow suspension decolorized within 10 minutes. The resulting solution was stirred for one hour and the solvent was then concentrated to 5 ml. A white solid precipitated out of the methanolic solution overnight, which was filtered, washed with methanol and then dried under reduced pressure (85 mg, 0.15 mmol, 52%).

¹H-NMR (400.1 MHz, CDCl₃): δ=6.86 (d, $^3J_{H,H}$=8.1 Hz, 2H), 6.51 (d, $^3J_{H,H}$=8.3 Hz, 1H), 6.40-6.33 (m, 5H), 6.25 (dd, $^3J_{H,H}$=8.3 Hz, $^2J_{H,H}$=2.5 Hz, 1H), 3.96 (q, $^3J_{H,H}$=7.0 Hz, 6H), 3.82 (d, $^2J_{H,H}$=13.4 Hz, 2H), 3.66 (d, $^2J_{H,H}$=13.4 Hz, 2H), 3.35 (s, 2H), 2.98-2.71 (m, 9H), 1.41-1.36 (m, 6H).

¹³C-NMR (100.6 MHz, CDCl₃): δ=160.4, 159.9, 159.2, 158.6, 129.7, 129.2, 114.3, 113.9, 106.4, 105.6, 102.6, 102.6, 63.5, 63.4, 62.5, 58.3, 57.9, 54.6, 49.4, 15.0.

MS (ESI pos., CH₃OH): m/z=588 ([M+Na]⁺, 100%), 566 ([M+H]⁺, 62%), 438 ([M-(CH₂—C₆H₄O—OC₂H₅)+Na]⁺, 25%), 416 ([M-(CH₂—C₆H₄O—OC₂H₅)+H]⁺, 46%).

EA [%] (C₃₂H₄₅N₃O₇.H₂O): C 65.49 (65.84), H 7.43 (7.77), N 7.27 (7.20).

Radiolabeling of ⁶⁸Ga

The cationically purified ⁶⁸Ga eluate (approx. 1600 MBq) from a ⁶⁸Ge/⁶⁸Ga generator (TiO₂, eluted with 0.6 M hydrochloric acid) was treated with 70 µL of a solution of TMeOHB-DAZA or TEOHB-DAZA (1 mg/ml in Ultrapur® water)/HCl (1 M)/ethanol, 3:1:1) and 2 ml of acetate buffer. The solution with a pH of 3.8-4.0 was heated at 100° C. for 5 minutes. The solution was then loaded onto a preconditioned C8 reversed-phase cartridge (SepPak®, C8 Plus), washed with 2 ml of water (water for injection), and the ⁶⁸Ga tracer eluted with 1 ml of ethanol (50%). The radiochemical yield was 65-80% (decay corrected). The sample was diluted with PBS (10 ml). The radiochemical purity was determined by radio-TLC and radio-HPLC and was ≥99.6%. The activities were determined in a calibrated activimeter.

Radiolabeling of X (⁶⁴Cu, ⁶⁷Ga, ¹¹¹In, ⁹⁹ᵐTc)

An aqueous solution of a compound I with addition of suitable additives or excipients such as buffers, reducing agents (e.g. SnCl₂), stabilizers, emulsifiers etc. and having a pH in a range of 2-12 is treated with an aqueous solution of radiometal X (⁶⁴Cu, ⁶⁷Ga, ¹¹¹In, ⁹⁹ᵐTc) having an activity of 1 MBq-100 GBq. The labeling is optionally carried out by heating to a temperature of up to 100° C. for 1 minute to 12 hours. The solution is then purified, concentrated, buffered or diluted so as to have a composition suitable for i.v. administration.

2. Administration in Ostrich Egg and PET/CT Examination

To carry out an intravascular injection in an embryonic egg, it is first necessary to find an amniotic blood vessel. This is done using a light-intensive Schier lamp (Tempo No. 119, Brecker Ltd. & Co. KG, Ruethen, Germany or Powerlux Eggtester 4.5 VDC, Lyon Technologies Inc., Chula Vista, Calif., USA), with which the egg is illuminated through the eggshell in similar manner to a diaphanoscopy. After locating a large-caliber vessel, an approximately 2.5×5 cm rectangular piece is machined from the approximately 2 mm thick egg shell (Dremel® 3000, Dremel Europe-Bosch Powertools B.V., Breda, the Netherlands). Particular care must be taken to maintain the intactness of the inner membrane of the eggshell, which corresponds to the chorioallantoic membrane (CAM).

After removing the eggshell lid—again using the Schier lamp—the yolk vessel is punctured with a narrow 27G cannula and this is fixed to the eggshell with adhesive strips. The access thus created now allows both CT contrast media and radiopharmaceuticals to be injected via a short length of plastic tubing (Smiths Medical™ 800/100/100 Smiths, Smiths Medical International Ltd, Ashford, Great Britain). To ensure this does not become occluded by blood flowing back and coagulating, it is flushed with heparin.

The tracers ⁶⁸Ga[TMeOHB-DAZA] and ⁶⁸Ga[TEOHB-DAZA] produced according to the described method were in each case injected in PBS solution through the access (approx. 10 MBq each, in 0.3-0.8 ml) and this was then immediately rinsed with 1 ml of isotonic saline (0.9%). The administration was carried out in list mode at the start time of the PET imaging procedure.

Summary of the Results of the Example Embodiments

The compounds of the formula I, TEOHB-DAZA and TMeOHB-DAZA, represent ligands that are suitable for labeling with ⁶⁸Ga and ⁶⁴Cu. Unlike with the known ligands EOB-DTPA and EHIDA, the ⁶⁸Ga complexes show no demetalation or decomposition in vivo. The ligands are stable and can be stored as precursors for labeling with ⁶⁸Ga or ⁶⁴Cu. Because of the small amounts of substance administered, no adverse toxicological effects are to be expected. The labeling of ⁶⁸Ga or ⁶⁴Cu for the synthesis of the complex is carried out according to standard radiopharmaceutical methods. The administration of ⁶⁸Ga-[TEOHB-DAZA] showed almost exclusive accumulation in the liver in the embryonated ostrich egg (in vivo in the incubated egg). A further advantage is the easy obtainability of the ligands TEOHB-DAZA and TMeOHB-DAZA starting from DAZA via an efficient one-pot synthesis in which only NaBH₄ as reducing agent is used.

REFERENCES

1. Greiser, J., Niksch, T., Freesmeyer, M. & Weigand, W. Investigations on the Ga(III) Complex of EOB-DTPA and Its 68Ga Radiolabeled Analogue. *J Vis Exp* (2016).
2. Greiser, J. et al. Synthesis and Characterization of Galli, InIII and LuII! Complexes of a Set of dtpa Bis-Amide Ligands. *Eur. J. Inorg. Chem.* 2015, 4125-4137, doi: 10.1002/ejic.201500436 (2015).
3. Price, E. W. & Orvig, C. Matching chelators to radiometals for radiopharmaceuticals. *Chem. Soc. Rev.* 43, 260-290, doi:10.1039/C3CS60304K (2014).
4. Price, T. W., Greenman, J. & Stasiuk, G. J. Current advances in ligand design for inorganic positron emission tomography tracers 68Ga, 64Cu, 89Zr and 44Sc. *Dalton Trans.*, Ahead of Print, doi:10.1039/C5DT04706D (2016).
5. Wadas, T. J., Wong, E. H., Weisman, G. R. & Anderson, C. Coordinating Radiometals of Copper, Gallium, Indium, Yttrium, and Zirconium for PET and SPECT Imaging of Disease. *J. Chem. Rev.* 110, 2858-2902 doi:10.1021/cr900325h. (2010).
6. Bartholoma, M. D., Louie, A. S., Valliant, J. F. & Zubieta, J. Technetium and Gallium Derived Radiopharmaceuticals: Comparing and Contrasting the Chemistry of Two Important Radiometals for the Molecular Imaging Era. *Chem. Rev.* (Washington, D.C., U.S.) 110, 2903-2920, doi:10.1021/cr1000755 (2010).
7. Clevette, D. J. & Orvig, C. Comparison of ligands of differing denticity and basicity for the in vivo chelation of aluminum and gallium. *Polyhedron* 9, 151-161, doi:10.1016/S0277-5387(00)80564-1 (1990).
8. Mathias, C. J. et al. Targeting radiopharmaceuticals: comparative biodistribution studies of gallium and indium complexes of multidentate ligands. *Nucl. Med. Biol.* 15, 69-81, doi:10.1016/0883-2897(88)90163-8 (1988).
9. Stroszczynski, C. et al. Current Status of MRI Diagnostics With Liver-Specific Contrast Agents. *Radiologe* 44, 1185, doi:10.1007/s00117-004-1134-5 (2004).

10. Vogl, T. J. et al. Liver tumors: comparison of MR imaging with Gd-EOB-DTPA and Gd-DTPA. *Radiology* 200, 59-67, doi:10.1148/radiology.200.1.8657946 (1996).
11. Weinmann, H. J. et al. A new lipophilic gadolinium chelate as a tissue-specific contrast medium for MRI. *Magn. Reson. Med.* 22, 233-237, doi:10.1002/mrm.1910220214 (1991).
12. Ba-Ssalamah, A. et al. MRT of the liver. *Radiologe* 44, 1170-1184, doi:10.1007/s00117-004-1142-5 (2004).
13. Reimer, P. et al. Phase II clinical evaluation of Gd-EOB-DTPA: dose, safety aspects, and pulse sequence. *Radiology* 199, 177-183, doi:10.1148/radiology.199.1.8633143 (1996).
14. Fritzberg, A. R. & Klingensmith, W. C., III. Quest for the perfect hepatobiliary radiopharmaceutical. *J. Nucl. Med.* 23, 543-546 (1982).
15. Haubner, R. et al. Development of (68)Ga-labelled DTPA galactosyl human serum albumin for liver function imaging. *Eur. J. Nucl. Med. Mol. Imaging* 40, 1245-1255 (2013).
16. Haubner, R. et al. [68Ga]NOTA-Galactosyl Human Serum Albumin: a Tracer for Liver Function Imaging with Improved Stability. *Mol. Imaging Biol.*, Ahead of Print, doi:10.1007/s11307-017-1046-1 (2017).
17. Choi, J. et al. Ga-68-labeled neolactosylated human serum albumin (LSA) for PET imaging of hepatic asialoglycoprotein receptor. *Nucl. Med. Biol.*, Ahead of Print, doi:10.1016/j.nucmedbio.2014.08.009 (2014).
18. Haubner, R. et al. [68Ga]NODAGA-RGD—Metabolic stability, biodistribution, and dosimetry data from patients with hepatocellular carcinoma and liver cirrhosis. *Eur. J. Nucl. Med. Mol. Imaging*, Ahead of Print, doi:10.1007/s00259-016-3396-3 (2016).
19. Ghosh, S., Das, T., Sarma, H. D. & Banerjee, S. Preparation and preliminary bioevaluation of 68Ga-oxine in lipiodol as a potential liver imaging agent. *J. Radioanal. Nucl. Chem.*, Ahead of Print, doi:10.1007/s10967-016-4985-0 (2016).
20. Burke, B. P. et al. Final step gallium-68 radiolabelling of silica-coated iron oxide nanorods as potential PET/MR multimodal imaging agents. *Faraday Discuss.* 175, 59-71, doi:10.1039/C4FD00137K (2014).
21. Pfeifer-Leeg, M. et al. Synthesis and Characterization of GaIII, YIII, and LuIII Complexes with Etifenin and Analogues. *Z. Anorg. Allg. Chem.* 642, 486-491, doi:10.1002/zaac.201600016 (2016).
22. Jurisson, S., Berning, D., Jia, W. & Ma, D. Coordination compounds in nuclear medicine. *Chem. Rev.* 93, 1137-1156, doi:10.1021/cr00019a013 (1993).
23. Romba, J. et al. The coordination chemistry of 1,4-diazepan-6-amine. *Eur. J. Inorg. Chem.*, 314-328, doi:10.1002/ejic.200500690 (2006).
24. Roesch, F., Waldron, B. P. & Parker, D. Bifunctional chelating agents based on the 1,4-diazepine scaffold (DAZA) for non-invasive molecular imaging. WO2014198478A2 (2014).
25. Tei, L., Gugliotta, G., Fekete, M., Kalman, F. K. & Botta, M. Mn(II) complexes of novel hexadentate AAZTA-like chelators: a solution thermodynamics and relaxometric study. *Dalton Trans.* 40, 2025-2032, doi:10.1039/c0dt01114b (2011).
26. Elemento, E. M., Parker, D., Aime, S., Gianolio, E. & Lattuada, L. Variation of water exchange dynamics with ligand structure and stereochemistry in lanthanide complexes based on 1,4-diazepine derivatives. *Org. Biomol. Chem.* 7, 1120-1131, doi:10.1039/b818445c (2009).
27. Aime, S. et al. [Gd-AAZTA]-: A New Structural Entry for an Improved Generation of MRI Contrast Agents. *Inorg. Chem.* 43, 7588-7590, doi:10.1021/ic0489692 (2004).
28. Baranyai, Z. et al. Equilibrium, Kinetic and Structural Studies of AAZTA Complexes with Ga3+, In3+ and Cu2+. *Eur. J. Inorg. Chem.* 2013, 147-162, doi:10.1002/ejic.201201108 (2013).
29. Baranyai, Z. et al. Equilibrium and kinetic properties of the lanthanoids (III) and various divalent metal complexes of the heptadentate ligand AAZTA. *Chem.-Eur. J.* 15, 1696-1705, doi:10.1002/chem.200801803 (2009).
30. Parker, D., Waldron, B. P. & Yufit, D. S. Crystallographic and solution NMR structural analyses of four hexacoordinated gallium(III) complexes based on ligands derived from 6-amino-perhydro-1,4-diazepine. *Dalton Trans.* 42, 8001-8008, doi:10.1039/c3dt50287b (2013).
31. Farkas, E. et al. Equilibrium, kinetic and structural properties of gallium(III)- and some divalent metal complexes formed with the new DATAm and DATA5m ligands. *Chemistry* (2017).
32. Vologdin, N., Rolla, G. A., Botta, M. & Tei, L. Orthogonal synthesis of a heterodimeric ligand for the development of the GdIII-GaIII ditopic complex as a potential pH-sensitive MRI/PET probe. *Org. Biomol. Chem.* 11, 1683-1690, doi:10.1039/c2ob27200h (2013).
33. Gugliotta, G., Botta, M. & Tei, L. AAZTA-based bifunctional chelating agents for the synthesis of multimeric/dendrimeric MRI contrast agents. *Org. Biomol. Chem.* 8, 4569-4574, doi:10.1039/c0ob00096e (2010).
34. Waldron, B. P. et al. Structure and stability of hexadentate complexes of ligands based on AAZTA for efficient PET labelling with gallium-68. *Chem. Commun.* (Cambridge, UK) 49, 579-581, doi:10.1039/C2CC37544C (2013).
35. Seemann, J. & al., e. Novel Ga-68-labeled folic acid derivatives. *Journal of Labelled Compounds and Radiopharmaceuticals* 56, 351 (2013).
36. Parker, D. & Waldron, B. P. Conformational analysis and synthetic approaches to polydentate perhydro-diazepine ligands for the complexation of gallium(III). *Org. Biomol. Chem.* 11, 2827-2838, doi:10.1039/c3ob40287h (2013).
37. Manzoni, L. et al. Synthesis of Gd and 68Ga Complexes in Conjugation with a Conformationally Optimized RGD Sequence as Potential MRI and PET Tumor-Imaging Probes. *ChemMedChem* 7, 1084-1093, doi:10.1002/cmdc.201200043 (2012).
38. Giovenzana, G. B. et al. Multidentate aza ligands able to complex metal ions and the their use in diagnostics and therapy. US20060034773A1 (2006).
39. Maiocchi, A., Visigalli, M., Beltrami, L., Sini, L. & Lattuada, L. A new class of diazepine derivative chelating agents and complexes with paramagnetic metals as MRI contrast agents. WO2013135750A1 (2013).
40. Giovenzana, G. B. et al. Multidentate aza ligands able to complex metal ions and the their use in diagnostics and therapy. WO2003008390A1 (2003).
41. Aime, S. et al. Contrast agents endowed with high relaxivity. WO2006002873A2 (2006).

42. Seemann, J., Waldron, B. P., Roesch, F. & Parker, D. Approaching 'Kit-Type' Labelling with 68Ga: The DATA Chelators. *ChemMedChem* 10, 1019-1026, doi: 10.1002/cmdc.201500092 (2015).

43. Madsen, S. L., Welch, M. J., Motekaitis, R. J. & Martell, A. E. Gallium-68-THM2BED: a potential generator-produced tracer of myocardial perfusion for positron emission tomography. *Nucl. Med. Biol.* 19, 431-444, doi: 10.1016/0883-2897(92)90158-U (1992).

44. Silva, F. et al. Chemical, radiochemical and biological studies of new gallium(III) complexes with hexadentate chelators. *Dalton Trans.* 44, 3342-3355, doi:10.1039/C4DT02274B (2015).

45. Sahoo, S. K., Kanungo, B. K. & Baral, M. Complexation of a tripodal amine-catechol ligand tris((2,3-dihydroxybenzylamino)ethyl)amine towards Al(III), Ga(III), and In(III). *Monatsh. Chem.* 140, 139-145, doi:10.1007/s00706-008-0068-4 (2009).

46. Liu, S., Rettig, S. J. & Orvig, C. Polydentate ligand chemistry of Group 13 metals: effects of the size and donor selectivity of metal ions on the structures and properties of aluminum, gallium, and indium complexes with potentially heptadentate (N4O3) amine phenol ligands. *Inorg. Chem.* 31, 5400-5407, doi: 10.1021/ic00052a015 (1992).

47. Caravan, P. & Orvig, C. Tripodal Aminophenolate Ligand Complexes of Aluminum(III), Gallium(III), and Indium(III) in Water. *Inorg. Chem.* 36, 236-248, doi: 10.1021/IC961222U (1997).

48. Higham, C. S. et al. Multidentate aminophenol ligands prepared with Mannich condensations. *Tetrahedron Lett.* 47, 4419-4423, doi:10.1016/j.tetlet.2006.04.077 (2006).

49. Huemmer, J., Heinemann, F. W. & Meyer, K. Uranium Tetrakis-Aryloxide Derivatives Supported by Tetraazacyclododecane: Synthesis of Air-Stable, Coordinatively-Unsaturated U(IV) and U(V) Complexes. *Inorg. Chem.*, Ahead of Print, doi:10.1021/acs.inorgchem.6b02123 (2016).

50. Wei, Y., Wang, G. & Wu, K. First Eu(II)/Ln(III) Mixed Complex with High Oxidative Stability. *Cryst. Growth Des.* 15, 5288-5292, doi:10.1021/acs.cgd.5b00804 (2015).

51. Wang, G., Wei, Y. & Wu, K. Goblet-shaped pentanuclear lanthanide clusters assembled with a cyclen derivative ligand exhibiting slow magnetic relaxation. *Dalton Trans.* 45, 12734-12738, doi:10.1039/C6D102062C (2016).

52. Nakai, H. et al. Control of Lanthanide Coordination Environment: Synthesis, Structure, and Oxygen-Sensitive Luminescence Properties of an Eight-Coordinate Tb(III) Complex. *Inorg. Chem.* 55, 6609-6615, doi: 10.1021/acs.inorgchem.6b00800 (2016).

53. Nakai, H. et al. A macrocyclic tetraamine bearing four phenol groups: a new class of heptadentate ligands to provide an oxygen-sensitive luminescent Tb(III) complex with an extendable phenol pendant arm. *Dalton Trans.* 44, 10923-10927, doi:10.1039/C5DT00816F (2015).

54. Bender, M. et al. Theoretically Predicted and Experimentally Observed Relaxation Pathways of two Heterodinuclear 3d-4f Complexes. *Z. Anorg. Allg. Chem.* 641, 2291-2299, doi:10.1002/zaac.201500595 (2015).

55. Moore, D. A., Fanwick, P. E. & Welch, M. J. Synthesis, characterization, and solid-state structure of a new hexachelating ligand and its complex with gallium (III). *Inorg. Chem.* 28, 1504-1506, doi:10.1021/ic00307a016 (1989).

56. Schnepf, R. et al. Resonance Raman Spectroscopic Study of Phenoxyl Radical Complexes. *J. Am. Chem. Soc.* 120, 2352-2364, doi:10.1021/JA972269X (1998).

57. Lam, O. P., Heinemann, F. W. & Meyer, K. A new diamantane functionalized tris(aryloxide) ligand system for small molecule activation chemistry at reactive uranium complexes. *C. R. Chim.* 13, 803-811, doi: 10.1016/j.crci.2010.03.004 (2010).

58. Murphy, B. P. et al. Lanthanide complexes of new ditopic, tripodal macrocycles:

synthetic, structural, stability and luminescence studies. *Inorg. Chem. Commun.* 5, 577-580, doi:10.1016/51387-7003(02)00486-0 (2002).

59. Schmidt, A.-C., Nizovtsev, A. V., Scheurer, A., Heinemann, F. W. & Meyer, K. Uranium-mediated reductive conversion of CO2 to CO and carbonate in a single-vessel, closed synthetic cycle. *Chem. Commun.* (Cambridge, UK) 48, 8634-8636, doi:10.1039/c2cc34150f (2012).

60. Adam, B. et al. Phenoxyl radical complexes of gallium, scandium, iron and manganese. *Chem.-Eur. J.* 3, 308-319, doi:10.1002/chem.19970030221 (1997).

61. Denat, F., Tripier, R., Boschetti, F., Espinosa, E. & Guilard, R. Reaction of polyamines with diethyloxalate: a convenient route for the synthesis of tetraazacycloalkanes. *ARKIVOC* (Gainesville, Fla., U.S.), 212-233, doi:10.3998/ark.5550190.0007.415 (2006).

62. Boyd, E. et al. Synthesis and derivatization of N,N'-trisubstituted 1,2-diamines derived from (1R,2R)-1,2-diaminocyclohexane. *Tetrahedron Lett.* 46, 3479-3484, doi:10.1016/j.tetlet.2005.03.129 (2005).

63. Zhang, Y. et al. Substituent-directed reduction of cyclic aminals leading to two different heterocycles selectively: syntheses of functionalized nicotines and pyrido[2,3-b]azepines. *Tetrahedron* 71, 1930-1939, doi:10.1016/j.tet.2015.02.025 (2015).

64. Yamamoto, H. & Maruoka, K. Regioselective carbonyl amination using diisobutylaluminum hydride. *J. Am. Chem. Soc.* 103, 4186-4194, doi:10.1021/ja00404a035 (1981).

65. Abdel-Magid, A. F., Carson, K. G., Harris, B. D., Maryanoff, C. A. & Shah, R. D.

Reductive Amination of Aldehydes and Ketones with Sodium Triacetoxyborohydride. Studies on Direct and Indirect Reductive Amination Procedures. *J. Org. Chem.* 61, 3849-3862, doi:10.1021/J0960057X (1996).

66. Mamedov, I., Engelmann, J., Eschenko, O., Beyerlein, M. & Logothetis, N. K. Dual-functional probes towards in vivo studies of brain connectivity and plasticity. *Chem. Commun.* (Cambridge, UK) 48, 2755-2757, doi:10.1039/C1CC15991G (2012).

67. Guanci, C. et al. Synthesis of phosphonic analogues of AAZTA=6-Amino-6-methylperhydro-1,4-diazepine-N,N',N",N"-tetraacetic acid and relaxometric evaluation of the corresponding Gd(III) complexes as potential MRI contrast agents. *Tetrahedron Lett.* 56, 1994-1997, doi:10.1016/j.tetlet.2015.02.118 (2015).

The invention claimed is:

1. A compound of the general formula I

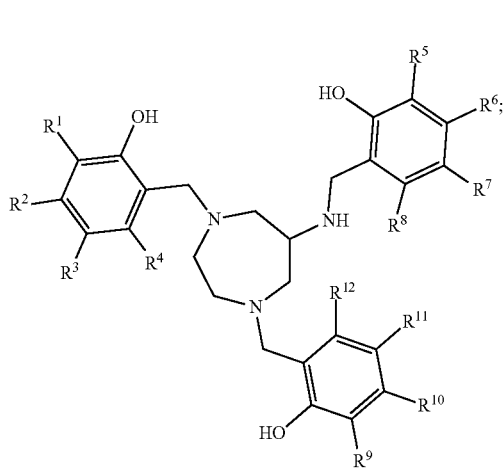

(I)

or a pharmaceutically acceptable salt of an inorganic or organic acid, a hydrate, a stereoisomer or a solvate thereof, including a radiolabeled complex thereof, where $R^1$, $R^2$, $R^3$, $R^4$, $R^5$, $R^6$, $R^7$, $R^8$, $R^9$, $R^{10}$, $R^{11}$, and $R^{12}$ are independently selected from hydrogen and alkoxy one or the substituents $R^1$, $R^2$, $R^3$, and $R^4$ is alkoxy and the other three substituents are hydrogen; and one of the substituents $R^5$, $R^6$, $R^7$, and $R^8$ is alkoxy and the other three substituents are hydrogen; and one of the substituents $R^9$, $R^{10}$, $R^{11}$, and $R^{12}$ is alkoxy and the other three substituents are hydrogen.

2. The compound as claimed in claim 1, wherein the radiolabeled complex consists of a compound of the formula I and a radioisotope selected from the group consisting of $^{68}$Ga, $^{64}$Cu, $^{67}$Ga, 111In, and $^{99m}$Tc, or is a complex corresponding to the general formula II:

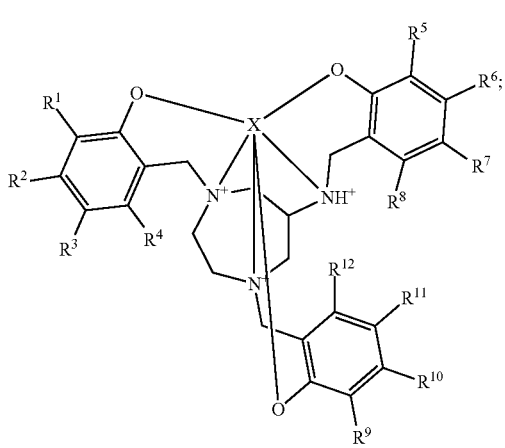

(II)

or a pharmaceutically acceptable salt of an inorganic or organic acid, a hydrate, a stereoisomer or a solvate thereof, where $R^1$, $R^2$, $R^3$, $R^4$, $R^5$, $R^6$, $R^7$, $R^8$, $R^9$, $R^{10}$, $R^{11}$, and $R^{12}$ are as defined in claim 1 and where X is selected from $^{68}$Ga, $^{67}$Ga, and $^{111}$In.

3. The compound as claimed in claim 1, where
$R^1$ is alkoxy and $R^2$, $R^3$, and $R^4$ are hydrogen; and
$R^5$ is alkoxy and $R^6$, $R^7$, and $R^8$ are hydrogen; and
$R^9$ is alkoxy and $R^{10}$, $R^{11}$, and $R^{12}$ are hydrogen;
or
$R^2$ is alkoxy and $R^1$, $R^3$, and $R^4$ are hydrogen; and
$R^6$ is alkoxy and $R^5$, $R^7$, and $R^8$ are hydrogen; and
$R^{10}$ is alkoxy and $R^9$, $R^{11}$, and $R^{12}$ are hydrogen;
or
$R^3$ is alkoxy and $R^1$, $R^2$, and $R^4$ are hydrogen; and
$R^7$ is alkoxy and $R^5$, $R^6$, and $R^8$ are hydrogen; and
$R^{11}$ is alkoxy and $R^9$, $R^{10}$, and $R^{12}$ are hydrogen;
or
$R^4$ is alkoxy and $R^1$, $R^2$, and $R^3$ are hydrogen; and
$R^8$ is alkoxy and $R^5$, $R^6$, and $R^7$ are hydrogen; and
$R^{12}$ is alkoxy and $R^9$, $R^{10}$, and $R^{11}$ are hydrogen.

4. The compound as claimed in claim 1, where
$R^2$ is alkoxy and $R^1$, $R^3$, and $R^4$ are hydrogen; and
$R^6$ is alkoxy and $R^5$, $R^7$, and $R^8$ are hydrogen; and
$R^{10}$ is alkoxy and $R^9$, $R^{11}$, and $R^{12}$ are hydrogen.

5. The compound as claimed in claim 4, where $R^2$, $R^6$, and $R^{10}$ are independently —O—$C_{1-12}$ alkyl and where the alkyl radical may be unbranched or branched.

6. The compound as claimed in claim 5, where $R^2$, $R^6$, and $R^{10}$ are independently selected from methoxy, ethoxy, propoxy, butoxy, pentoxy, heptoxy, hexoxy and octoxy.

7. The compound as claimed in claim 1, where $R^2$, $R^6$, and $R^{10}$ are ethoxy.

8. The compound as claimed in claim 1, where $R^2$, $R^6$, and $R^{10}$ are methoxy.

9. The compound as claimed in claim 1, wherein the compound is selected from tris-N,N',N''(4-ethoxy-2-hydroxybenzyl)-1,4-diazepan-6-amine and tris-N,N',N''(4-methoxy-2-hydroxybenzyl)-1,4-diazepan-6-amine.

10. The compound as claimed in claim 2, wherein the compound is selected from
$^{68}$Ga[tris-N,N',N''(4-ethoxy-2-hydroxybenzyl)-1,4-diazepan-6-amine],
$^{68}$Ga[tris-N,N',N''(4-methoxy-2-hydroxybenzyl)-1,4-diazepan-6-amine],
$^{64}$Cu[tris-N,N',N''(4-ethoxy-2-hydroxybenzyl)-1,4-diazepan-6-amine],
$^{64}$Cu[tris-N,N',N''(4-methoxy-2-hydroxybenzyl)-1,4-diazepan-6-amine],
$^{67}$Ga[tris-N,N',N''(4-ethoxy-2-hydroxybenzyl)-1,4-diazepan-6-amine],
$^{67}$Ga[tris-N,N',N''(4-methoxy-2-hydroxybenzyl)-1,4-diazepan-6-amine],
$^{111}$In[tris-N,N',N''(4-ethoxy-2-hydroxy-benzyl)-1,4-diazepan-6-amine],
$^{111}$In[tris-N,N',N''(4-methoxy-2-hydroxybenzyl)-1,4-diazepan-6-amine],
$^{99m}$Tc[tris-N,N',N''(4-ethoxy-2-hydroxybenzyl)-1,4-diazepan-6-amine],
$^{99m}$Tc[tris-N,N',N''(4-methoxy-2-hydroxybenzyl)-1,4-diazepan-6-amine],
$^{68}$Ga[tris-N,N',N''(3-ethoxy-2-hydroxybenzyl)-1,4-diazepan-6-amine],
$^{68}$Ga[tris-N,N',N''(5-ethoxy-2-hydroxybenzyl)-1,4-diazepan-6-amine],
$^{68}$Ga[tris-N,N',N''(6-ethoxy-2-hydroxybenzyl)-1,4-diazepan-6-amine],
$^{68}$Ga[tris-N,N',N''(3-methoxy-2-hydroxybenzyl)-1,4-diazepan-6-amine],
$^{68}$Ga[tris-N,N',N''(5-methoxy-2-hydroxybenzyl)-1,4-diazepan-6-amine],
$^{68}$Ga[tris-N,N',N''(6-methoxy-2-hydroxybenzyl)-1,4-diazepan-6-amine], $^{64}$Cu[tris-N,N',N"(3-ethoxy-2-hydroxybenzyl)-1,4-diazepan-6-amine],
$^{64}$Cu[tris-N,N',N"(5-ethoxy-2-hydroxybenzyl)-1,4-diazepan-6-amine],
$^{64}$Cu[tris-N,N',N"(6-ethoxy-2-hydroxybenzyl)-1,4-diazepan-6-amine],
$^{64}$Cu[tris-N,N',N"(3-methoxy-2-hydroxybenzyl)-1,4-diazepan-6-amine],
$^{64}$Cu[tris-N,N',N"(5-methoxy-2-hydroxybenzyl)-1,4-diazepan-6-amine],
$^{64}$Cu[tris-N,N',N"(6-methoxy-2-hydroxybenzyl)-1,4-diazepan-6-amine],
$^{67}$Ga[tris-N,N',N"(3-ethoxy-2-hydroxybenzyl)-1,4-diazepan-6-amine],
$^{67}$Ga[tris-N,N',N"(5-ethoxy-2-hydroxybenzyl)-1,4-diazepan-6-amine],
$^{67}$Ga[tris-N,N',N"(6-ethoxy-2-hydroxybenzyl)-1,4-diazepan-6-amine],
$^{67}$Ga[tris-N,N',N"(3-methoxy-2-hydroxybenzyl)-1,4-diazepan-6-amine],
$^{67}$Ga[tris-N,N',N"(5-methoxy-2-hydroxybenzyl)-1,4-diazepan-6-amine],
$^{67}$Ga[tris-N,N',N"(6-methoxy-2-hydroxybenzyl)-1,4-diazepan-6-amine],
$^{111}$In[tris-N,N',N"(3-ethoxy-2-hydroxybenzyl)-1,4-diazepan-6-amine],
$^{111}$In[tris-N,N',N"(5-ethoxy-2-hydroxybenzyl)-1,4-diazepan-6-amine],
$^{111}$In[tris-N,N',N"(6-ethoxy-2-hydroxybenzyl)-1,4-diazepan-6-amine],
$^{111}$In[tris-N,N',N"(3-methoxy-2-hydroxybenzyl)-1,4-diazepan-6-amine],
$^{111}$In[tris-N,N',N"(5-methoxy-2-hydroxybenzyl)-1,4-diazepan-6-amine],
$^{111}$In[tris-N,N',N"(6-methoxy-2-hydroxybenzyl)-1,4-diazepan-6-amine],
$^{99m}$Tc[tris-N,N',N"(3-ethoxy-2-hydroxybenzyl)-1,4-diazepan-6-amine],
$^{99m}$Tc[tris-N,N',N"(5-ethoxy-2-hydroxybenzyl)-1,4-diazepan-6-amine],
$^{99m}$Tc[tris-N,N',N"(6-ethoxy-2-hydroxybenzyl)-1,4-diazepan-6-amine],
$^{99m}$Tc[tris-N,N',N"(3-methoxy-2-hydroxybenzyl)-1,4-diazepan-6-amine],
$^{99m}$Tc[tris-N,N',N"(5-methoxy-2-hydroxybenzyl)-1,4-diazepan-6-amine], and
$^{99m}$Tc[tris-N,N',N"(6-methoxy-2-hydroxybenzyl)-1,4-diazepan-6-amine].

11. The compound as claimed in claim 2, wherein the compound is selected from
$^{68}$Ga[tris-N,N',N"(4-ethoxy-2-hydroxybenzyl)-1,4-diazepan-6-amine],
$^{68}$Ga[tris-N,N',N"(4-methoxy-2-hydroxybenzyl)-1,4-diazepan-6-amine],
$^{64}$Cu[tris-N,N',N"(4-ethoxy-2-hydroxybenzyl)-1,4-diazepan-6-amine], and
$^{64}$Cu[tris-N,N',N"(4-methoxy-2-hydroxybenzyl)-1,4-diazepan-6-amine].

12. A pharmaceutical or radiopharmaceutical composition comprising a compound of the formula I or of the formula II as claimed in claim 2 and one or more pharmaceutically acceptable diluents or vehicles.

13. The pharmaceutical or radiopharmaceutical composition as claimed in claim 12, comprising PBS-buffered saline.

14. A kit for preparing a radiopharmaceutical preparation, wherein the kit comprises a sealed ampoule containing a predetermined amount of a compound of the formula I or of the compound of the formula II and optionally instructions for using the components of the kit, wherein formula I is:

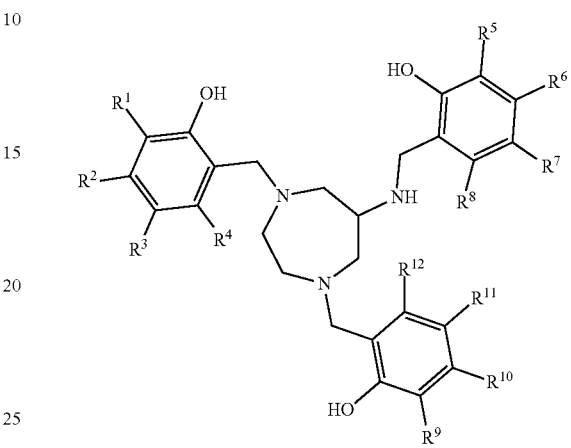

where $R^1$, $R^2$, $R^3$, $R^4$, $R^5$, $R^6$, $R^7$, $R^8$, $R^9$, $R^{10}$, $R^{11}$, and $R^{12}$ are independently selected from hydrogen and alkoxy, and formula II is:

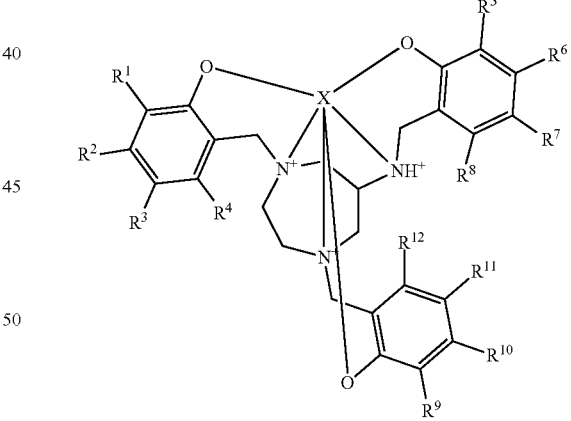

where X is selected from $^{68}$Ga, $^{67}$Ga, and $^{111}$In, wherein
one of the substituents $R^1$, $R^2$, $R^3$, and $R^4$ is alkoxy and the other three substituents are hydrogen: and
one of the substituents $R^5$, $R^6$, $R^7$, and $R^8$ is alkoxy and the other three substituents are hydrogen: and
one of the substituents $R^9$, $R^{10}$, $R^{11}$, and $R^{12}$ is alkoxy and the other three substituents are hydrogen.

15. A method for preparing a compound of the general formula I as claimed in claim 1, comprising the steps of a) synthesizing a compound of the formula III

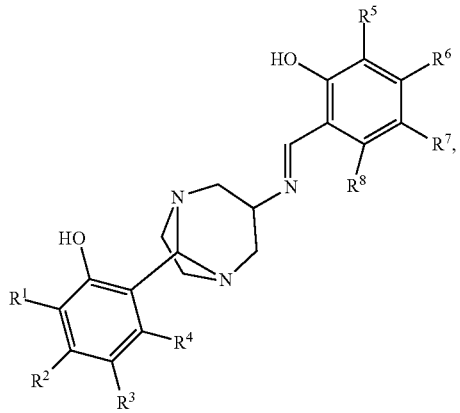

where $R^1$, $R^2$, $R^3$, $R^4$, $R^5$, $R^6$, $R^7$, and $R^8$ are as defined in claim 1;

through reaction of a compound of the formula IV

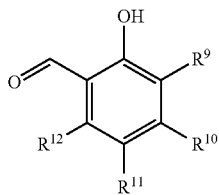

where $R^9$, $R^{10}$, $R^{11}$, and $R^{12}$ are as defined in claim 1, with a compound of the formula (V):

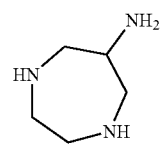

in the presence of a suitable solvent, such as methanol; and b) reacting the compound of the formula III under reducing conditions with a suitable reducing agent in the presence of a suitable solvent.

16. A method for preparing a compound of the general formula II as claimed in claim 2 comprising treating a compound of the formula I with a $^{68}$Ga-containing solution at a pH of 5.0 or lower or with a $^{64}$Cu-containing-solution at a pH of 4.0 or higher.

17. The method as claimed in claim 16, wherein the method is carried out at 50° C. or higher.

18. A method for obtaining an image of the liver of an animal or human, wherein the method comprises the following steps:
   (a) administering to an animal or human a pharmaceutical composition comprising a compound of the formula II as claimed in claim 2,
   (b) carrying out a PET or a PET/CT scan of the treated animal or human;
   (c) detecting a measurable emission signal due to the compound of the formula II from the animal or human concerned; and
   (d) generating an image from the detectable signal, thereby obtaining an image of the liver of the animal or human.

19. The compound of the formula II as claimed in claim 2, wherein the compound accumulates selectively in the liver.

20. The pharmaceutical composition as claimed in claim 12, wherein the composition has an activity of at least 50 MBq.

21. The pharmaceutical composition as claimed in claim 12, wherein the composition has a stability of at least 98% for at least 4 hours in human serum and PBS-buffered saline.

* * * * *